United States Patent
Zhang et al.

(10) Patent No.: US 6,437,281 B1
(45) Date of Patent: Aug. 20, 2002

(54) APPARATUS, SYSTEM, AND RELATED METHOD FOR SENSING A CHARACTERISTIC OF A WORKPIECE IN AN AUTOMATED PROCESS

(75) Inventors: YuMing Zhang, 2636 Fireside Cir., Lexington, KY (US) 40513; Pengjiu Li, Lexington, KY (US); Shaobin Zhang, 700 Woodland Ave. Apt. G-309, Lexington, KY (US) 40508

(73) Assignees: YuMing Zhang; Shaobin Zhang, both of Lexington, KY (US)

( * ) Notice: Subject to any disclaimer, the term of this patent is extended or adjusted under 35 U.S.C. 154(b) by 0 days.

(21) Appl. No.: 09/631,162

(22) Filed: Aug. 3, 2000

Related U.S. Application Data

(60) Provisional application No. 60/147,331, filed on Aug. 5, 1999.

(51) Int. Cl.[7] .............................................. B23K 10/00
(52) U.S. Cl. .............................. 219/121.45; 219/121.54
(58) Field of Search ........................... 219/121.45, 118, 219/121.54, 121.34, 130.32, 121.39, 121.58, 121.48, 121.37; 266/67–72; 700/258

(56) References Cited

U.S. PATENT DOCUMENTS

| | | |
|---|---|---|
| 2,921,179 A | 1/1960 | Anderson |
| 3,017,496 A | 1/1962 | Greene |
| 3,021,419 A | 2/1962 | Rascati et al. |
| 3,278,720 A | 10/1966 | Dixon |
| 4,119,828 A | 10/1978 | Bykhovsky et al. |
| 4,169,224 A | 9/1979 | Puschner |
| 4,242,620 A | 12/1980 | Fujiwara et al. |
| 4,410,786 A | 10/1983 | Cloos |
| 4,477,713 A | 10/1984 | Cook et al. |
| 4,531,192 A | 7/1985 | Cook |
| 4,570,049 A | 2/1986 | Albert et al. |
| 5,302,799 A | 4/1994 | Kennedy et al. |
| 5,463,201 A | 10/1995 | Hedengren et al. |

FOREIGN PATENT DOCUMENTS

FR          901867 A2 *   3/1999

OTHER PUBLICATIONS

S.M. Govardham et al., "Real–Time Welding Process Control Using Infrared Sensing", Proceedings of the American Control Conference, pp. 1712–1716, Jun. 1995.

(List continued on next page.)

*Primary Examiner*—Mark Paschall
*Assistant Examiner*—Quang Van
(74) *Attorney, Agent, or Firm*—King & Schickli, PLLC

(57) ABSTRACT

An apparatus, system and related method are disclosed for sensing a characteristic of a workpiece, such as the location of a welding seam, using a sensor that is independent of another device for performing an operation on the workpiece, such as a welding torch for welding a seam. The sensor preferably takes the form of a plasma arc torch. This plasma arc torch travels along the workpiece, preferably just ahead of the welder for welding the workpiece or other implement and simultaneously moves to and fro in a direction transverse to the direction of travel of the welder. A non-transferred electrical arc serves to ionize a plasma gas issuing from the plasma arc torch to create a concentrated plasma jet directed towards the workpiece. By sensing a characteristic of the plasma jet as the plasma arc torch moves to and fro and the workpiece is traversed, such as the change in voltage across a sensing circuit including the plasma jet itself, the location of a seam or other physical characteristic associated with the workpiece (i.e., a hole, plate, or the like) may be detected.

20 Claims, 7 Drawing Sheets

OTHER PUBLICATIONS

S.B. Zhang et al., "Noncontact Ultrasonic Sensing for Seam Tracking in Arc Welding Processes", Transactions of the ASME, vol. 120, pp. 600–608, Aug. 1998.

L. Li et al., "Plasma Charge Sensor for In–Process, Non–Contact Monitoring of the Laser Welding Process", Meas. Sci. Technol. 7, pp. 615–626, 1996.

George E. Cook, "Robotic Arc Welding: Research in Sensory Feedback Control", IEEE Transactions on Industrial Electronics, vol. IE–30, No. 3, pp. 252–268, Aug. 1983.

J. W. Kim et al., "A Study on an Arc Sensor for Gas Metal Arc Welding of Horizontal Fillets", Welding Research Supplement, pp. 216–221, Aug. 1991.

Je–Yong Yu et al., "A Study of Vision Sensors for Seam Tracking of Height–Varying Weldment. Part 1: Mathematical Model", Mechatronics, vol. 7, No. 7, pp. 599–612, 1997.

Ajay Mahajan et al., "Intelligent Seam Tracking Using Ultrasonic Sensors for Robotic Welding", Robotica, vol. 15, pp. 275–281, 1997.

* cited by examiner

APPARATUS, SYSTEM, AND RELATED METHOD FOR SENSING A CHARACTERISTIC OF A WORKPIECE IN AN AUTOMATED PROCESS

This application claims the benefit of U.S. Provisional Patent Application Ser. No. 60/147,331, entitled "Non-transferred plasma arc based sensor for seam tracking," filed Aug. 5, 1999, which is incorporated herein by reference.

TECHNICAL FIELD

The present invention relates generally to the sensor art and, more particularly, to a sensor for sensing the location of a physical characteristic of workpiece on which an automated process or like operation is being performed.

BACKGROUND OF THE INVENTION

In automated welding systems, the ability of the welder to reliably track a seam or other physical characteristic associated with a workpiece is a fundamental and exceedingly important requirement. Various types of contact and non-contact sensors have been proposed to locate the weld seam and/or measure the weld joint. However, non-contact sensors are generally preferred for most applications, since interference with the workpiece is avoided.

In the past, others have proposed various types of non-contact sensors, including for example "through-the-arc" and machine vision sensors. In "through-the-arc" sensors, the location of the seam or other physical characteristic of the workpiece is determined by evaluating a characteristic, such as the arc length, of a transferred electrical arc formed between a welding torch, or more specifically the electrode associated therewith, and the workpiece. One example of a transferred arc sensor is found in U.S. Pat. No. 4,531,192 to Cook, the disclosure of which is incorporated herein by reference.

Transferred arc sensors have a few desirable characteristics when used in practical automated welding systems. For instance, sensing function is generally unaffected by the light projecting from the arc, heat radiation, and spattering. Another desirable characteristic is that no specialized hardware is required, since the transferred arc produced by the welding torch or electrode itself provides the sensing function. This keeps manufacturing and operating costs relatively low. In addition, the performance of a transferred arc sensor does not, in general, depend on either the surface conditions or the material forming the workpiece.

Despite these beneficial characteristics, transferred arc sensors do have some significant limitations and shortcomings. For example, to locate the seam, transferred arc sensors must "weave" to and fro across the workpiece. Since the sensing function is provided by the same arc used to weld the workpiece, this weave creates interference with the welding process and may not always be permissible or desirable. Also, for welding processes employing a consumable electrode, such as gas metal arc welding (GMAW) the arc length generally varies due to the continuous transfer of droplets of molten metal from the end of the electrode. This variable arc length creates a highly variable arc voltage signal, which of course significantly complicates locating the weld seam.

Further, due to the distribution of the electric welding arc in conventional GMAW or similar welding techniques where a transferred arc is established between the welding torch and the workpiece, the tracking resolution is usually relatively great (i.e., one millimeter or greater). Moreover, in a transferred arc arrangement, the anode spot (that is, the spot where the transferred electrical arc makes contact with the workpiece) tends to move, or "jump," from place to place because of the minimum arc principle. Of course, this "jump" makes it difficult to locate the edges of small seams having narrow root openings with any degree of precision.

Compared with transferred arc sensors, machine vision sensors employing cameras are less process-dependent and create less interference with the welding process. A high tracking resolution is also possible, depending on the field of view and type of camera used. In addition to seam tracking, the camera may also be used to obtain detailed information about the profile of the joint geometry for use in advanced process control.

However, machine vision sensors are quite sensitive to environmental conditions, such as the light projecting from the arc, metal spatters, surface shine of the workpiece, and orientation. Also, the hardware required, including the camera, is expensive and the maintenance costs are relatively high. All of these shortcomings make machine vision sensors generally undesirable for use in basic automated welding operations.

Accordingly, a need is identified for an improved sensor for sensing a characteristic of a workpiece, such a weld seam, in an automated process, such as a welding operation. The sensor would provide reliable sensing function despite the presence of arc light, heat radiation, spatters, surface shine, or variations in the type of material forming the workpiece. In automated welding, the sensor would operate independently of the welding process itself, thereby avoiding the problems associated with conventional transferred arc sensors. The sensor would also have sufficient accuracy/tracking resolution to identify the seam for many different joint designs, including the common square butt joint, as well as to precisely locate edges, holes, inclines/declines, etc. The sensor would also use existing technology, would be inexpensive to produce, implement and maintain, and would also have a reasonably long service life.

SUMMARY OF THE INVENTION

An apparatus, system and related method are disclosed for sensing a characteristic of a workpiece, such as the location of a welding seam, using a sensor that is independent of another device for performing an operation on the workpiece, such as a welder. In the most preferred embodiment, a plasma arc torch serves as the sensor. This torch travels along the workpiece during the automated welding operation, preferably just ahead of the welder for welding a seam formed in the workpiece, and moves to and fro in a direction substantially transverse to the direction of travel of the welder. A non-transferred electrical pilot arc is established on the plasma arc torch, such as the electrode and a constricting nozzle in the conventional plasma arc welding arrangement. As is known in the art, this non-transferred arc serves to ionize a plasma gas issuing from the torch to create a concentrated plasma jet that is capable of conducting current. This plasma jet is directed towards the workpiece, usually by an orifice in the constricting nozzle. By sensing a characteristic of the plasma jet as the workpiece is traversed, such as the change in voltage across the sensing circuit that includes the plasma jet as a resistive element, the location of a seam or other physical characteristic (i.e., a hole, plate, or the like) may be determined. As should be appreciated, the stiffness and concentration of the constricted plasma jet significantly improves the tracking resolution, making it possible to sense narrow seams having small root openings (i.e., one millimeter or less). Also, since no electrical arc is transferred, no anode spot is created on the workpiece. Thus, deleterious anode spot "jumping" is avoided and the dependence on the minimum arc principle is eliminated. Also, the proposed sensor advantageously operates independently of the welding process, and thus can be applied to various welding processes, such as arc welding, including plasma arc welding and short-circuiting transfer, without significant modification of the basic hardware and software employed.

In accordance with a first aspect of the present invention, an apparatus for sensing a physical characteristic associated with a workpiece is provided. The apparatus includes a sensor for directing a plasma jet toward the workpiece and a first motive device for moving the sensor relative to the workpiece in a first direction. The physical characteristic of the workpiece is sensed by observing changes in a reference characteristic of the plasma jet. Based on this sensed physical characteristic, an automated process, such as a welding operation, may be controlled.

Preferably, the sensor is a plasma arc torch positioned adjacent to a welder for welding the workpiece. The plasma arc torch includes a non-transferred pilot arc for ionizing a plasma gas to generate the plasma jet. A second motive device is also provided for moving the welder in a second direction, with the first direction being substantially transverse to the second direction. In one embodiment, the reference characteristic is a change in voltage across a circuit including the plasma jet. The apparatus also preferably includes a controller, such as a computer or other processor, for controlling at least the second direction based on an observed change in voltage. The physical characteristic of the workpiece is preferably the location of a seam, and the first direction of travel is substantially transverse to the seam. The first motive device also includes a motor for laterally translating a support for the plasma arc torch to and fro along the first direction of travel. Instead of a seam, the physical characteristic of the workpiece may also be the presence of an element positioned on the workpiece (i.e., a plate or the like) or an edge of the workpiece.

In an alternate embodiment, the welder and plasma arc torch are concentric, and the plasma arc torch rotates at least partially around the welder to provide sensing function. Specifically, a second motive device is provided for moving the welder along the workpiece in a second direction, and a second motive device is provided for rotating the plasma arc torch at least partially around the welder.

In accordance with a second aspect of the present invention, a system for automatically welding a workpiece is provided. The system comprises a welder for welding the workpiece, a sensor coupled to the welder for directing a plasma jet toward the workpiece, a first motive device for moving the sensor in a first direction, a second motive device for moving at least one of the welder or the workpiece in a second variable direction, with the first direction being substantially transverse to the second direction, and a controller, such as a computer or other processor, for controlling the second direction based on sensed changes in a reference characteristic of the plasma jet. The reference characteristic is preferably a voltage across a sensing circuit including at least the plasma jet as a resistive element. Preferably, the plasma jet is generated by a plasma arc torch having a non-transferred pilot arc positioned in advance of the welder. The sensor is preferably positioned in advance of the welder, and the two may be concentric.

In accordance with a third aspect of the present invention, a method of sensing a physical characteristic of a workpiece is disclosed. The method includes directing a plasm jet towards the workpiece, moving at least one of the plasma jet or the workpiece, sensing a change in a reference characteristic of the plasma jet, and sensing a physical characteristic of the workpiece based on the sensed change in the reference characteristic of the plasma jet. In a preferred embodiment, the plasma jet is established by a plasma arc torch, and the method further includes positioning the plasma jet torch in advance of a welder for welding a seam on the workpiece. Also, the step of moving is preferably moving the plasma jet and includes transversely scanning the plasma jet torch across the seam. The reference characteristic is preferably a voltage across a circuit including at least the plasma jet as a resistive element, and the method further includes determining a direction of travel for moving the welder along the seam based on changes in the sensed voltage. In one embodiment, the welder and plasma arc torch are concentric, and scanning is completed by rotating the plasma arc torch at least partially around the welder. The location of the seam is then determined based on the sensed changes in the reference voltage.

BRIEF DESCRIPTION OF THE DRAWING FIGURES

DETAILED DESCRIPTION OF THE INVENTION

Figure 1:
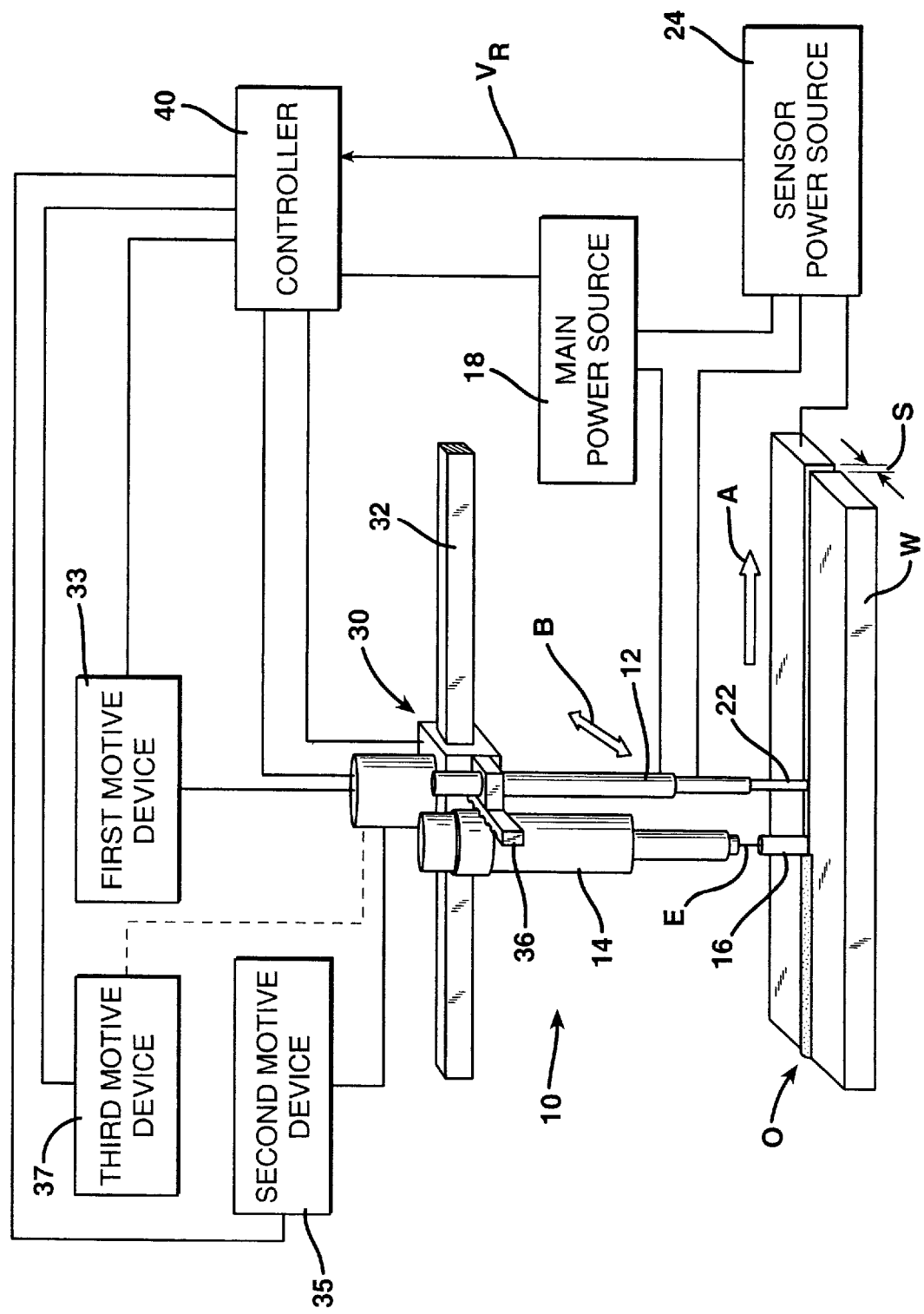
FIG. 1 is a schematic diagram showing an exemplary setup of a system for performing automated welding that uses a plasma arc torch as a sensor for creating a plasma jet, a characteristic of which is observed to sense a physical characteristic of the workpiece, such as the location of a weld seam.

Reference is now made to FIG. 1, which is a schematic diagram showing one possible embodiment of an automated system 10 for welding a workpiece W, such as between two pieces of metal positioned adjacent to each other or in an abutting relationship to define a seam S. The illustrated system 10 includes a sensor in the form of a plasma arc torch 12 positioned in advance of a welder, which is shown as a welder 14, also referred to as a welding torch, having a consumable electrode E. As is well-known in the art, this electrode E is caused to melt by the heat of a transferred arc 16 generated between it and the workpiece W using power supplied by a power source (not shown) to produce droplets of molten metal that together create a weld pool. Upon solidifying, this weld pool creates a welded joint between the two portions of the workpiece W defining the seam S. Although a torch 14 having a consumable electrode E and using a transferred arc 16 is shown for purposes of describing one particularly preferred embodiment, it should be appreciated that the sensor of the present invention may be used in conjunction with any type of welding apparatus (i.e., GMAW, GTAW, plasma arc, etc.), and may even be used in conjunction with other devices for performing an operation on a workpiece other than welding, such as a cutter, painter, or the like. Examples of several possible applications to which a sensor of the type disclosed may be employed can be found in the above-referenced Cook '192 patent, and additional, detailed descriptions of various types of welding methods can be found in U.S. Pat. Nos. 6,013,896, 6,008,470, and 5,990,446, all to Zhang, the disclosures of which are also incorporated herein by reference.

Figure 2A:
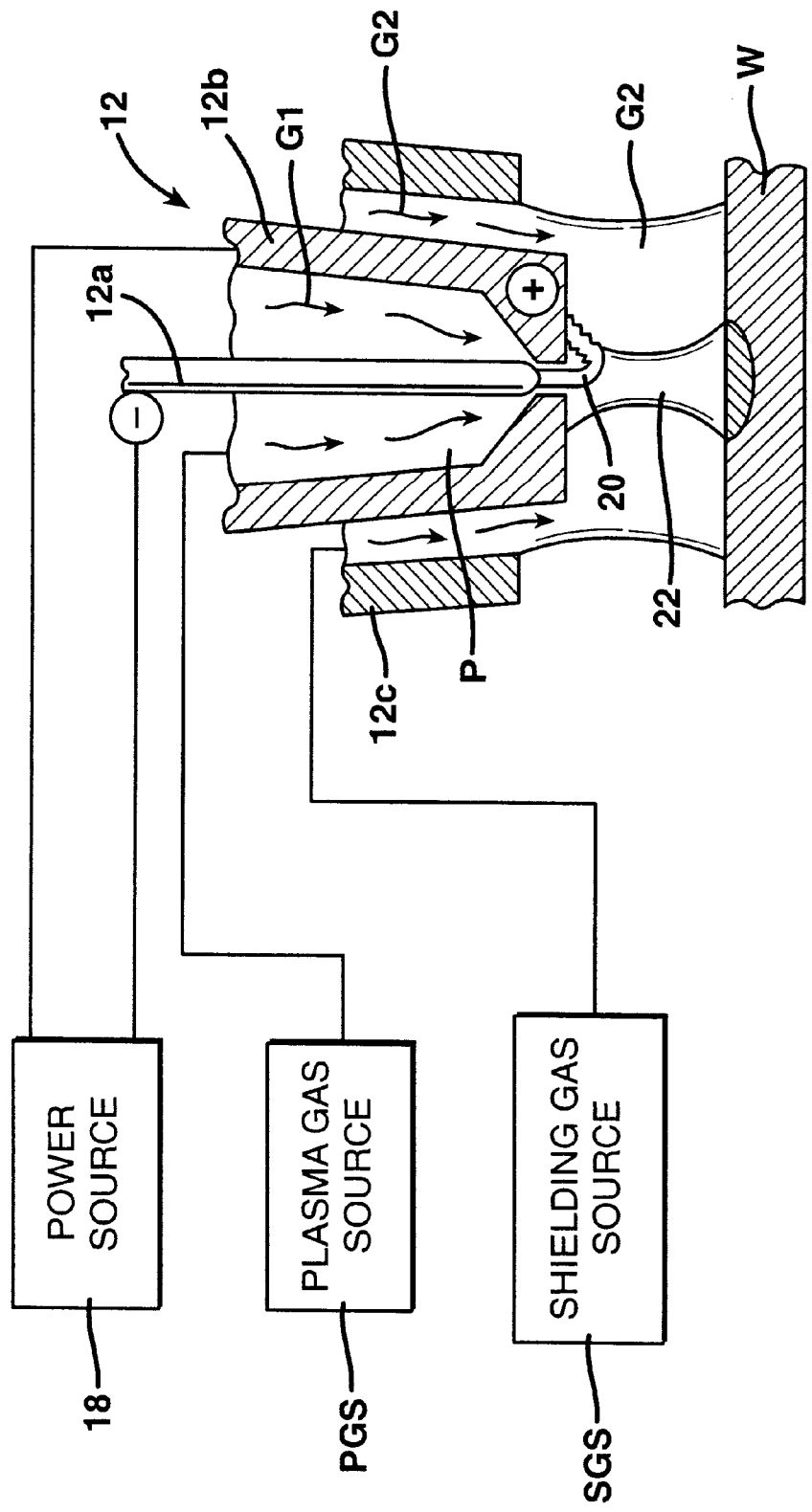
FIG. 2a is a partially cutaway, partially schematic diagram of a plasma arc torch wherein a non-transferred arc is used to ionize a plasma gas and create a plasma jet and direct the jet toward the workpiece.
Figure 2B:
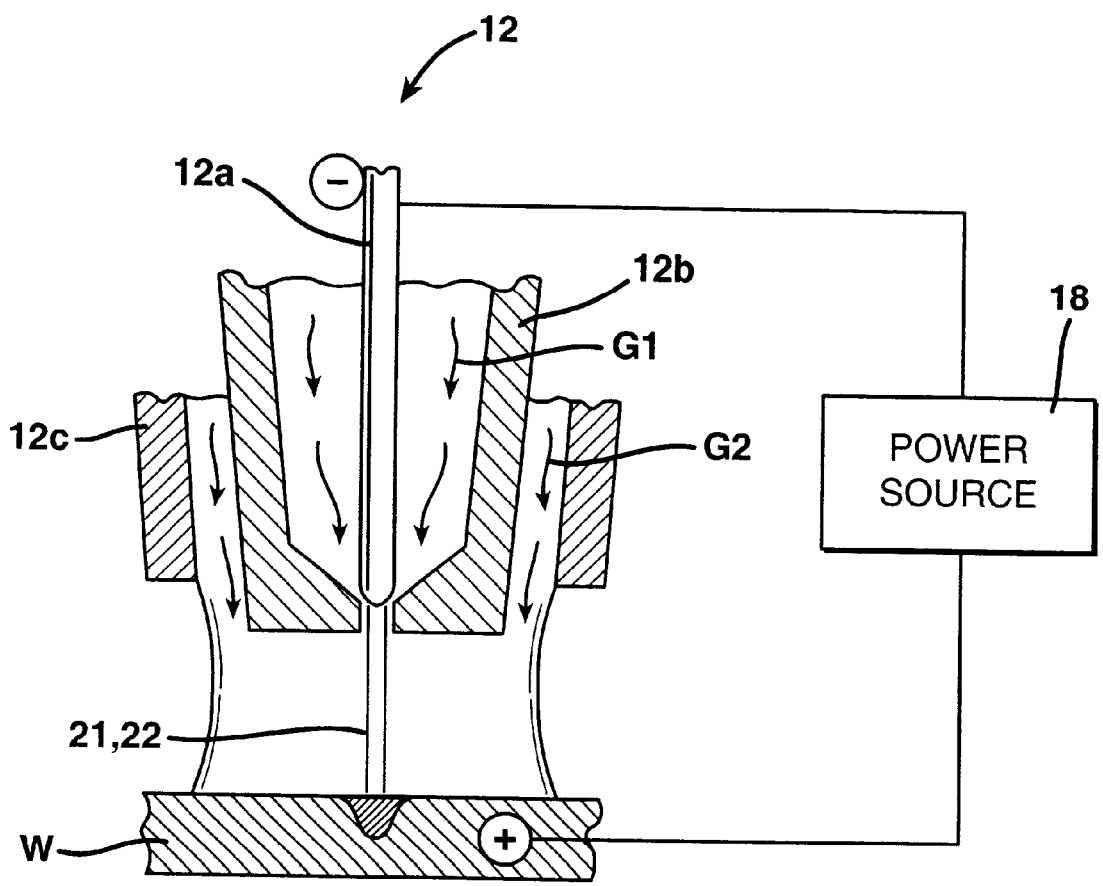
FIG. 2b is a partially cutaway, partially schematic diagram of a plasma arc torch wherein a transferred arc is used to ionize a plasma gas to create a transferred plasma arc.

With reference to FIG. 2a, the basic operation of a plasma arc torch 12 is shown. The torch 12 comprises a non-consumable electrode 12a surrounded by a constricting nozzle 12b. Together, the electrode 12a and constricting nozzle 12b define a plenum P that directs the flow of plasma gas $G_1$ supplied by a plasma gas source PGS toward the workpiece W. In a conventional plasma arc torch 12, the constricting nozzle 12b is surrounded by a shielding gas nozzle 12c that likewise directs the flow of a gas $G_2$ for shielding the plasma jet 22. This shielding gas $G_2$ is supplied by a shielding gas source SGS and issues from the torch 12 toward the workpiece W. A first power source 18 preferably having a constant voltage is also provided for generating a non-transferred electrical pilot arc 20. Specifically, the negative lead or connection from the power source 18 is connected to the electrode 12a, while the positive lead is connected to the constricting nozzle 12b. This creates a pilot arc 20 that extends between the electrode 12a and the constricting nozzle 12b. This pilot arc 20 serves to ionize the plasma gas $G_1$ issuing from the orifice in the constricting nozzle 12b, which creates a constricted, highly concentrated plasma jet 22 (also sometimes referred to as a non-transferred plasma arc, thus indicating that the electrical pilot arc 20 is not transferred to the workpiece W). This jet 22 is capable of conducting electricity and in conventional plasma welding operations is usually protected from atmospheric interference or contamination by the shielding gas $G_2$ (although the use of a shielding gas supplied apart from the torch 12 is also possible). As should be appreciated by those of skill in the art, this "non-transferred" arrangement is in contrast to the "transferred" arc arrangement, as shown in FIG. 2b, wherein the positive lead of the power source 18 is connected to the workpiece W, rather than the constricting nozzle 12b. In addition to a plasma jet 22, this arrangement creates an electrical arc 21 between the distal end of the electrode 12a and workpiece W itself, which is thus termed a transferred arc.

Figure 3:
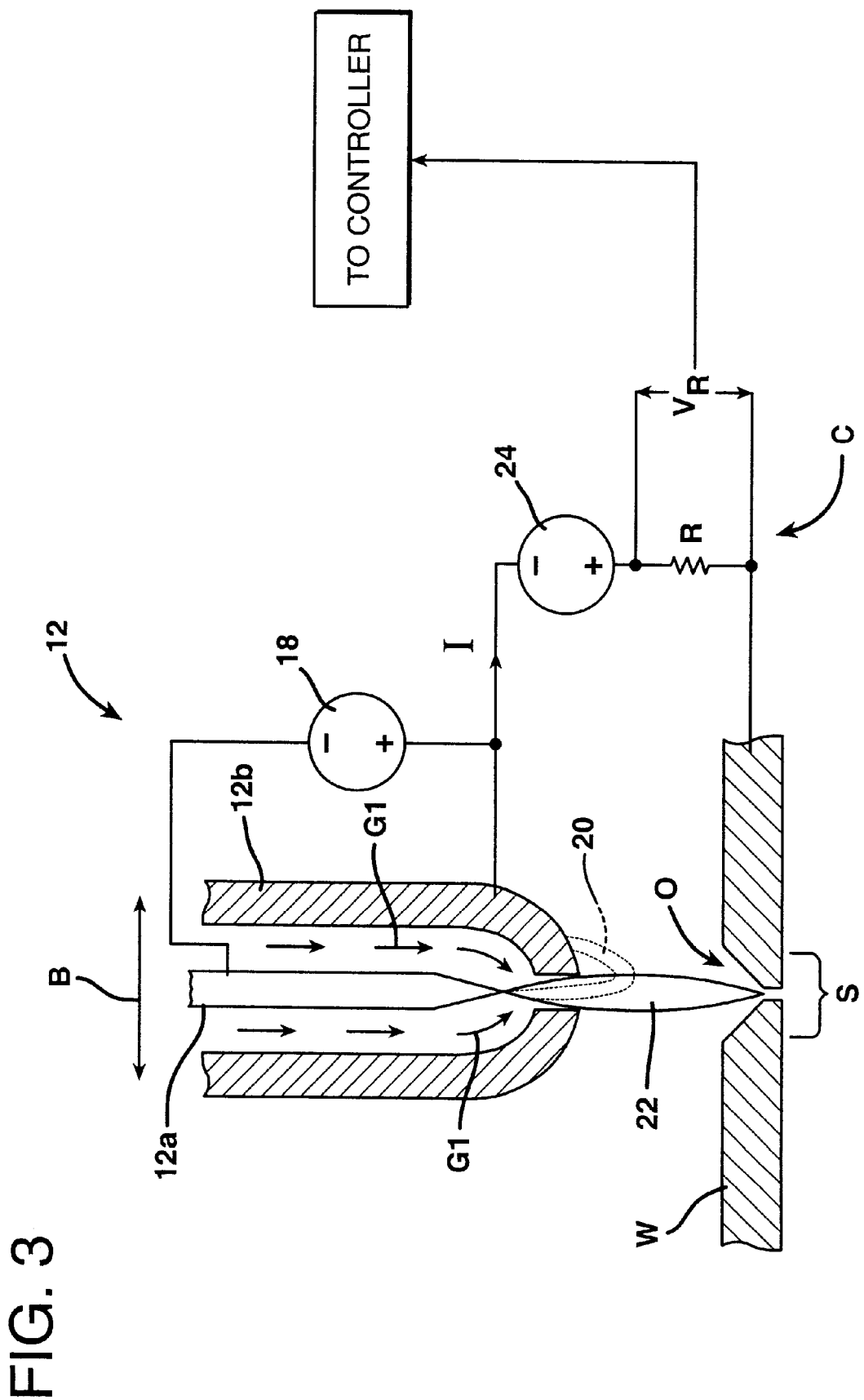
FIG. 3 is a partially cutaway, partially schematic diagram of a plasma arc torch having a non-transferred arc used in the most preferred embodiment, also illustrating in particular the manner in which main and sensor power sources are connected to the sensor or plasma arc torch and the workpiece in the most preferred embodiment.

FIG. 3 illustrates the manner in which power is supplied to the plasma arc torch 12 used as the sensor in the most preferred embodiment. The constant voltage power source 18 used in this particularly preferred embodiment for generating the non-transferred pilot arc 20 is connected between the non-consumable electrode 12a and the constricting nozzle 12b, substantially as described in the foregoing paragraph. Since the plasma jet 22 of the sensor plasma arc torch 12 is not used to actually weld the workpiece W, it should be appreciated that the shielding gas nozzle 12c and corresponding shielding gas source SGS may be eliminated. Additionally, a second power source 24 preferably also having a constant voltage, is connected between the constricting nozzle 12b and the workpiece W. This second power source 24 defines a part of a sensing circuit C that also includes the ionized gas forming the plasma jet 22. Preferably, the voltage provided by the power source 24 is selected such that the "loop" current I traveling along the sensing circuit C is low. This low current I thus does not interfere with the creation of the pilot arc 20, which in the illustrated embodiment relies on the constricting nozzle 12b as well. A resistor R may also form a part of the sensing circuit C. The resistance is selected to magnify the relatively low "loop" current I and hence the output voltage across the resistor R that is sensed.

As should be appreciated, the flow of current I along the sensing circuit C creates a change in a reference voltage measured across the resistor R, referred to as $V_R$, the magnitude of which is dependent on the length of the plasma jet 22. More specifically, as the length of the plasma jet 22 increases, such as when it extends into a root opening ) of the seam S in the workpiece W (or into a hole, over an edge, or down a decline), the overall resistance of the circuit C increases. This of course decreases the reference voltage $V_R$ for a known current I flowing through the sensing circuit C. Conversely, when the length of the plasma jet 22 decreases, such as when a plate (not shown) positioned on the workpiece W or other inclination is contacted, the overall resistance of the sensing circuit C decreases. By monitoring the increase or drop in voltage $V_R$ in the sensing circuit C, such as between the workpiece W and the constricting nozzle 12b through the plasma jet 22 (i.e., across the resistor R), a transitional characteristic of the workpiece W may be sensed, as demonstrated in the examples that follow.

With reference back to FIG. 1, it is thus possible to use the sensor of the present invention in conjunction with an automated system 10 for welding or performing an operation on a workpiece W. In the illustrated embodiment, the torch 12 forming the plasma arc sensor and the welder 14 are both separately connected to a support mechanism 30. Preferably, the sensor torch 12 is mounted sufficiently far ahead of the welder 14 to avoid creating any turbulence that might affect the welding operation (i.e, about 25 millimeters). The support mechanism 30 is capable of translating to and fro along a support beam 32 positioned adjacent to the workpiece W. The support mechanism 30 preferably comprises or is coupled to a first motive device 33, such as a conventional DC motor (not shown) for moving both the plasma arc torch 12 and welder 14 along the beam 32 in the direction of action arrow A. The support mechanism 30 also includes a second motive device 35, such as a stepper motor (not shown), for moving a rack 36 carrying the plasma arc torch 12 to and fro across the workpiece W in a direction substantially transverse to the seam S and the direction of travel of the support mechanism 30 (see action arrow B). This allows the plasma jet 22 to "scan" to and fro across the seam S, with each pass creating changes in voltage $V_R$. The measured changes in voltage $V_R$ (or its magnitude alone) may be observed, or provided to a controller 40, such as a computer or other processor. The controller 40 may then generate a corresponding signal for controlling an optional third motive device 37, such as a stepper motor (not shown) forming a part of the support mechanism 30 for moving the welder 14 itself transversely relative to the seam S such that automated tracking may occur. Of course, a possible equivalent arrangement is to hold the welder 14 or other device stationary while a single motive device (not shown) moves the workpiece W or an associated fixture based on the sensed voltage change $V_R$.

Figure 4A:
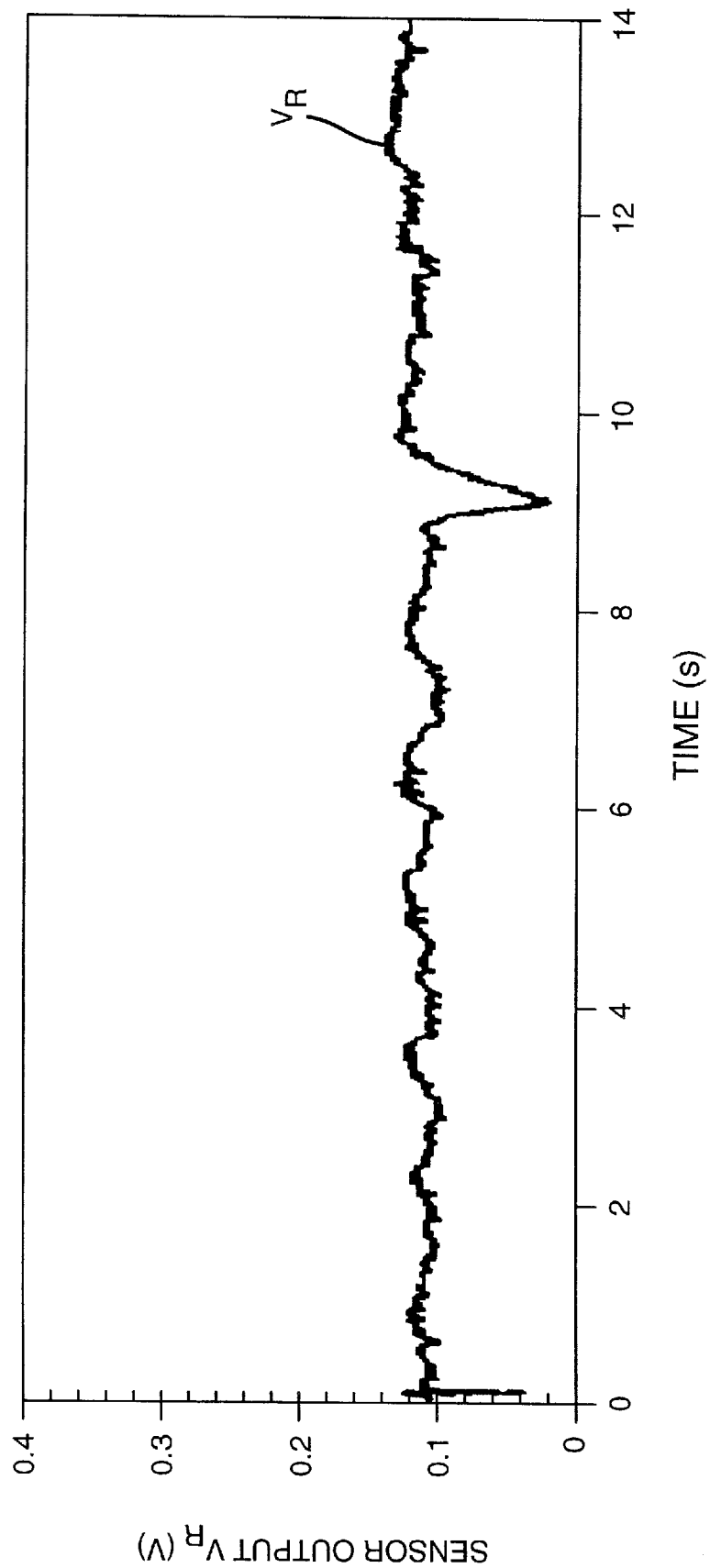
FIG. 4a is a graphical representation of an output reference voltage over time of a sensor circuit including at least the plasma jet as a resistive element when scanning a root opening.
Figure 4B:
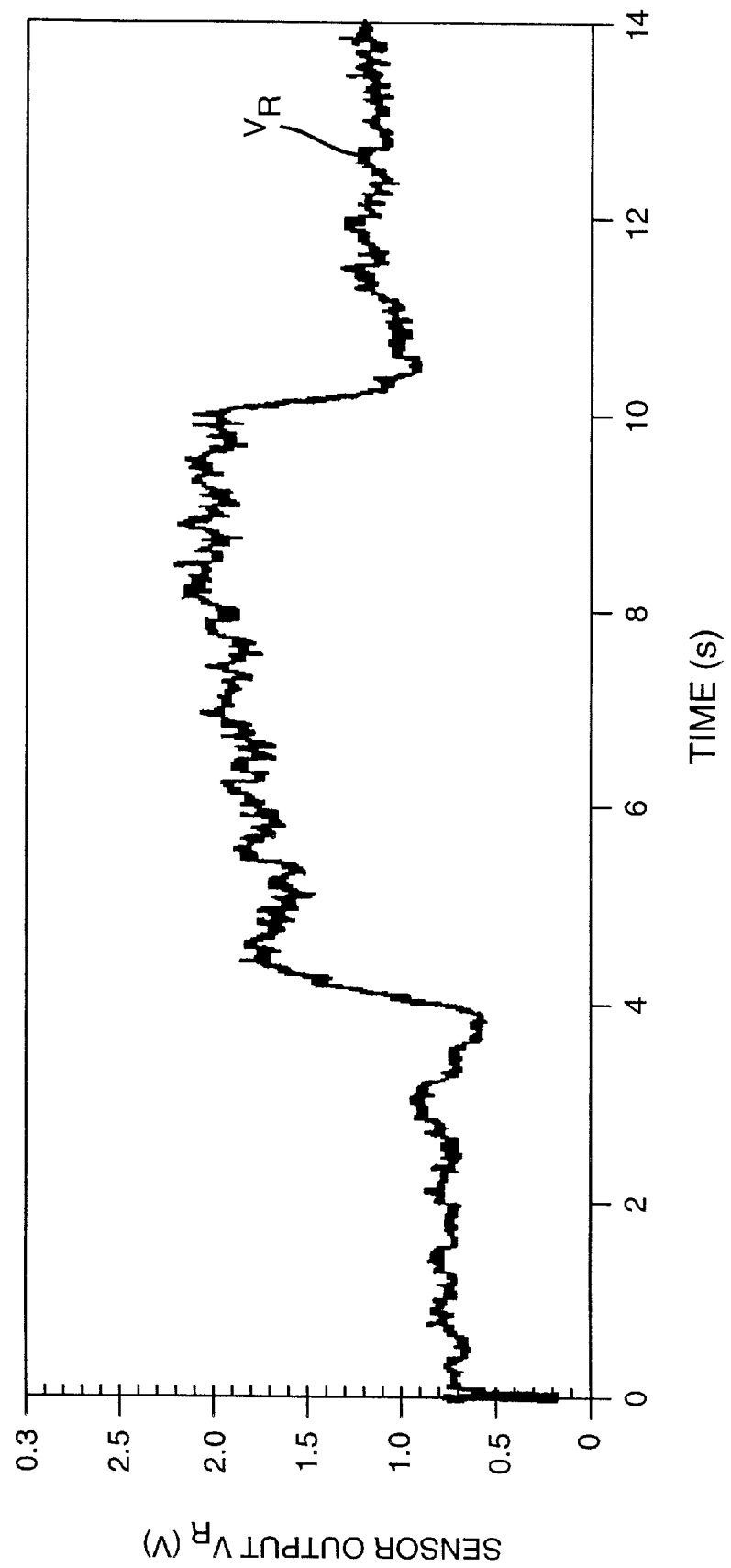
FIG. 4b is a graphical representation of an output reference voltage over time of a sensor circuit including at least the plasma jet as a resistive element when scanning a substantially flat plate placed on a workpiece.

FIGS. 4a and 4b illustrate graphically the results of experiments performed using the set-up substantially as disclosed in FIG. 1, with the plasma arc torch 12 and the welder 14 being supported by a "weaver" module, such as Model No. MDS-1005 produced by Bug-O Systems. Specifically referring to FIG. 4a, the current of the pilot arc 20 for purposes of the first experiment is 15 amps and the plasma gas $G_1$ (which as well known in the art may be argon, argon mixed with helium, or other suitable gas mixture) is issued at a relatively low rate, such as 1.2 L/min (3 ft$^3$/hour). The constant voltage power source 24 produces 24 volts of electricity and the resistance of the resistor R is 10 ohms. This creates a loop current I in the sensing circuit C of less than one ampere. The root opening O of the seam S is approximately one millimeter in width, and the scanning speed of the sensor is 10 millimeters per second.

Despite this relatively narrow seam S, the position at which the plasma jet 22 moves over the V-shaped root opening O can easily be determined from viewing the graph. Of course, by supplying the information on the changes in the voltage change $V_R$ to a software control algorithm or the like, the controller 40 may make adjustments to the direction of travel of the support mechanism 30 (i.e., the "weaver" module) to ensure that the welder 14 automatically and properly tracks the seam S.

In FIG. 4b, the plasma arc torch 12 is moved over a substantially flat plate (not shown) positioned on the workpiece W. The plate has a thickness of approximately 0.6 millimeters and a length in the scan direction (action arrow A) of approximately 60 millimeters. The scanning speed of the sensor is again 10 millimeters per second, and the other parameters are substantially as described in the first example.

The transitions of the voltage change $V_R$ (which is actually an increase in view of the fact that the length of the plasma jet 22 is reduced by the contacting the plate) at the edges of the plate are clearly identifiable from the graph. Again, by sensing the changes in voltage $V_R$, the controller 40 may control the movement of the support mechanism 30 such that a corresponding operation, such as welding, is performed along the edges of the plate resting on the workpiece W.

Figure 5:
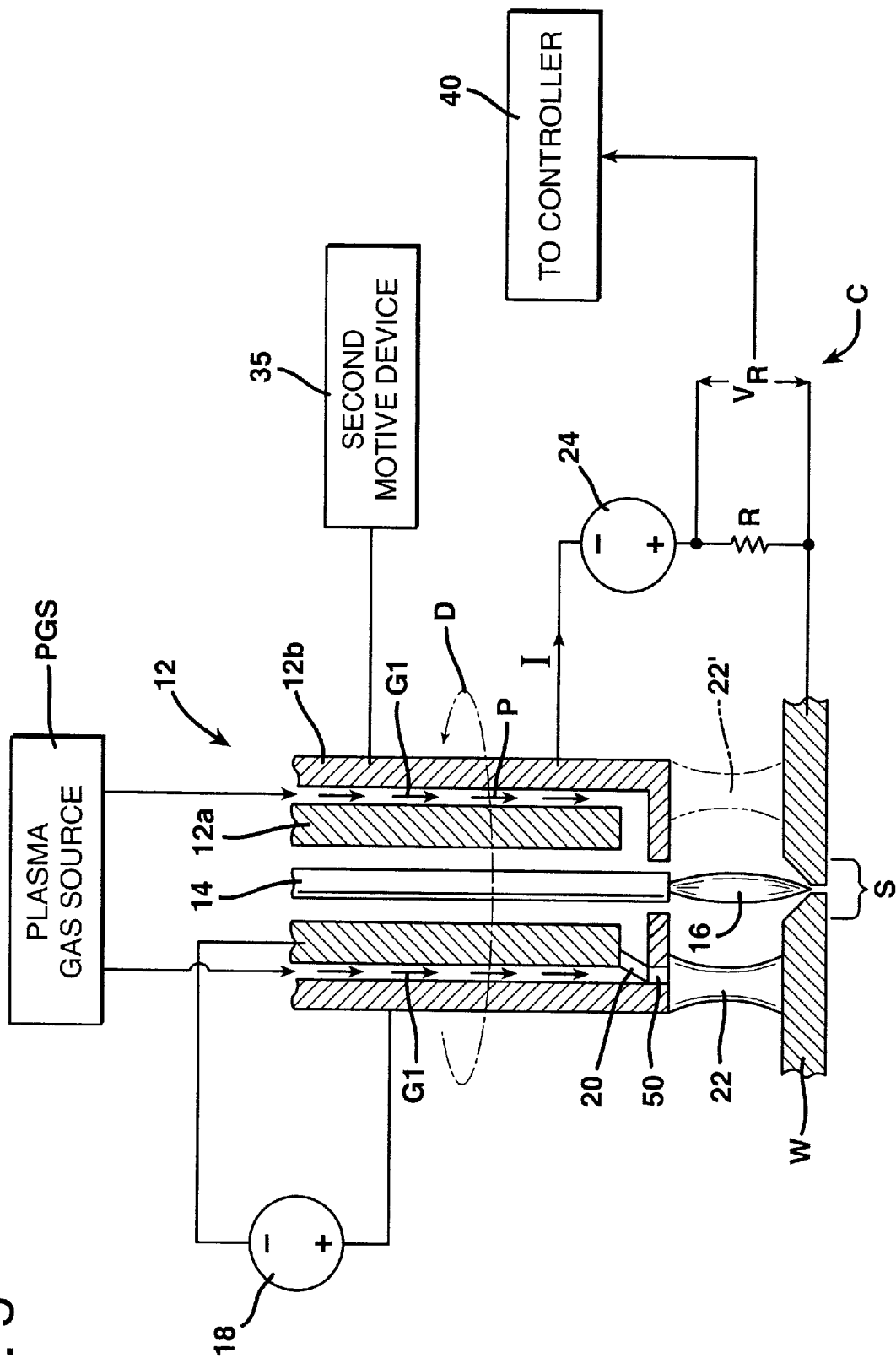
FIG. 5 shows an alternate embodiment of the sensor of the present invention.

One possible alternate embodiment of the sensor of the present invention is shown in FIG. 5. In this embodiment, the sensor also takes the form of a plasma arc torch 12. However, instead of being positioned in advance of a welder 14, the plasma arc torch 12 completely surrounds it such that the two are substantially concentric. The torch 12 includes a cylindrical inner wall 12a and concentric cylindrical outer wall 12b that together define a plenum P for receiving a plasma gas from plasma gas source PGS. Preferably, at least the outer wall 12b is rotatably mounted relative to the inner wall 12a of the welder 14, which is shown as being comprised of a single electrode for establishing a transferred arc 16 with the workpiece W using power supplied by a third power source (not shown). The electrode may be consumable or non-consumable. The positive lead of a power source 18 is connected to the outer wall 12b, while the negative lead is attached to the inner wall 12a, such that a non-transferred electric arc 20 is established. Similar to the embodiment shown in FIG. 1, this arc 20 ionizes the plasma gas $G_1$, which issues from at least one aperture 50 formed in the bottom portion of the outer wall 12b in the form of a plasma jet 22. To enhance the stability of the plasma jet 22, as well as to prevent contamination of the weld pool created by the welder 14, a shielding gas may also be supplied from an external source (not shown).

By rotating at least the outer wall 12b around the welder 14, or more specifically, the electrode, as it moves along the workpiece W in a first variable direction, such as along a weld seam S, the plasma jet 22 moves or scans across the workpiece (see action arrow D and the phantom rendering of the plasma jet 22' on the right hand side of FIG. 5). By observing the voltage change $V_R$ (increase or drop) across the resistor R in the sensing circuit C including the plasma jet 22 substantially as described above and sending a corresponding signal to a controller 40, the location of the seam S may be determined and an adjustment made to the direction of travel of the welder 14 to ensure that proper automatic tracking occurs. The motive force for moving both the torch 12 and the welder 14 along the workpiece W may be provided by a first motive device, such as the automated welding system illustrated in FIG. 1, while the rotational motion for at least the outer wall 12b of the torch 12 may be provided by a second motive device 35. In one contemplated embodiment, motive device 35 includes a source of pressurized gas for issuing an inert gas or gas mixture, such as air, against a wing-like vane (not shown) projecting outwardly from the outer wall 12b of the torch 12. As should be appreciated, the force of the gas contacting this vane causes the rotatably mounted outer wall 12b to rotate around the torch 14 at a certain angular velocity. The rotation distance may be through any range up to and including 360°, and may either reciprocate or continuously rotate around the welder 14, as necessary desired for a particular workpiece geometry.

The foregoing description of a preferred embodiment of the apparatus, system, and method of the present invention has been presented for purposes of illustration and description. It is not intended to be exhaustive or to limit the invention to the precise form disclosed. Obvious modifications or variations are possible in light of the above teachings, including the substitution of any known type of welder or other device for performing an operation on a workpiece that is conducive to automation (i.e., painting, cutting, sanding, etc.). The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An apparatus for sensing a physical characteristic associated with a workpiece, comprising:

a sensor for directing a plasma jet toward the workpiece;

a first motive device for moving the sensor relative to the workpiece in a first direction;

whereby the physical characteristic of the workpiece is sensed by observing changes in a reference characteristic of the plasma jet.

2. The apparatus according to claim 1, further including a welder for welding the workpiece, and wherein said sensor is a plasma arc torch positioned adjacent to said welder, said plasma arc torch including a non-transferred pilot arc for ionizing a plasma gas to create said plasma jet.

3. The apparatus according to claim 2, further including:

a second motive device for moving the welder along the workpiece in a second variable direction;

wherein said first direction is substantially transverse to the second direction.

4. The apparatus according to claim 3, wherein said reference characteristic is a change in voltage across a circuit including the plasma jet, and further including a controller for controlling at least the second direction of travel based on the voltage change.

5. The apparatus according to claim 4, wherein the characteristic of the workpiece is a location of a seam, and said first direction is substantially transverse to the seam.

6. The apparatus according to claim 5, wherein the first motive device includes a motor for laterally translating a support for said plasma arc torch to and fro along said first direction.

7. The apparatus according to claim 4, wherein the physical characteristic of the workpiece is the presence of an element positioned on the workpiece.

8. The apparatus according to claim 4, wherein the physical characteristic is an edge of the workpiece.

9. The apparatus according to claim 2, wherein the welder and plasma arc torch are concentric.

10. The apparatus according to claim 9, wherein the plasma arc torch rotates at least partially around the welder.

11. The apparatus according to claim 10, further including:

a second motive device for moving the welder along the workpiece in a first direction;

wherein said first motive device rotates the plasma arc torch at least partially around the welder.

12. A system for automatically welding a workpiece, comprising:

a welder for welding the workpiece;

a sensor coupled to the welder for directing a plasma jet toward the workpiece;

a first motive device for moving the sensor in a first direction;

a second motive device for moving at least one of the welder or the workpiece in a second variable direction, said first direction being substantially transverse to the second direction; and a controller for controlling at least the second direction based on sensed changes in a reference characteristic of said plasma jet.

13. The system according to claim 12, wherein said reference characteristic is a voltage across a sensing circuit including the plasma jet.

14. The system according to claim 12, wherein the plasma jet is generated by a plasma arc torch having a non-transferred pilot arc positioned in advance of the welder.

15. The system according to claim 12, wherein the welder is concentric with the sensor.

16. The system according to claim 12, wherein the controller is a computer.

17. A method of sensing a physical characteristic of a workpiece, comprising:

directing a plasma jet towards the workpiece;

moving at least one of the plasma jet or the workpiece;

sensing a change in a reference characteristic of the plasma jet;

sensing a physical characteristic of the workpiece based on the sensed change in the reference characteristic of the plasma jet.

18. The method of claim 17, wherein the plasma jet is established by a plasma arc torch, and further including positioning the plasma arc torch in advance of a welder for welding a seam on the workpiece.

19. The method of claim 18, wherein the step of moving is moving the plasma jet and includes scanning the plasma arc torch transversely across the seam and said reference characteristic is a voltage across a circuit including at least the plasma jet as a resistive element, further including determining a direction of travel for moving the welder along the seam based on changes in the sensed voltage.

20. The method of claim 19, wherein the welder and plasma arc torch are concentric, and further including rotating the plasma arc torch at least partially around the welder and determining the location of the seam based on the sensed changes in the reference voltage.

* * * * *